United States Patent [19]

Alonso

[11] Patent Number: 5,032,128
[45] Date of Patent: Jul. 16, 1991

[54] HEART VALVE PROSTHESIS

[75] Inventor: Manuel T. Alonso, Newport Beach, Calif.

[73] Assignee: Medtronic, Inc., Minneapolis, Minn.

[21] Appl. No.: 216,571

[22] Filed: Jul. 7, 1988

[51] Int. Cl.$^5$ .............................................. A61F 2/24
[52] U.S. Cl. ........................................ 623/2; 623/900
[58] Field of Search .................................... 623/2, 900

[56] References Cited

U.S. PATENT DOCUMENTS

| | | | |
|---|---|---|---|
| 3,997,923 | 12/1976 | Possis | 3/1.5 |
| 4,535,483 | 8/1985 | Hawtley | 623/2 |
| 4,561,129 | 12/1985 | Aupesella | 623/2 |
| 4,680,031 | 7/1987 | Alonso | 623/2 |
| 4,705,516 | 11/1987 | Barone | 623/2 |
| 4,759,758 | 7/1988 | Gabbay | 623/2 |
| 4,790,843 | 12/1988 | Caupentier | 623/2 |

OTHER PUBLICATIONS

Bartek et al., "Frame-Mounted Tissue Heart Valves: Technique of Construction", Thorax, (1974), 29, 51.
Article, "A New Bioprosthesis for Aortic and Mitral Valve Replacement: Preliminary Evaluation of the Tascon Valve", published in *Texas Heart Institute Journal*, 14(1):31-38, Mar. 1987.
Article, "Surgical Aspects of Valve Implantation: Tascon Heart Valve Bioprosthesis", in Moise, D., Steiner, R. M., Fernandez, J., (eds): Guide to Prosthetic Cardiac Valves, New York, Springer-Verlag, 1985, pp. 149-150.
Article, "Initial Experimental Experience with a 'Replaceable' Cardiac Valve Prosthesis", by Cooper et al., published in the *Annals of Thoracic Surgery*, 45:554-558, May 1988.

*Primary Examiner*—David J. Isabella
*Assistant Examiner*—David H. Willse
*Attorney, Agent, or Firm*—Robert J. Klepinski

[57] ABSTRACT

A heart valve prosthesis and method for replacement of the same are disclosed. The prosthesis includes a sewing ring for permanent attachment to heart tissue, and a valve assembly which is replaceably mounted within the sewing ring in a spaced-apart relationship to define a cylindrical cutting path therebetween. The valve assembly is attached to the sewing ring by interconnecting sutures, but the cylindrical cutting path is otherwise devoid of structure which projects therebetween. Thus, replacement of the valve assembly can be accomplished by insertion of a cutting member, such as a thin scalpel blade, within the cylindrical cutting path, thereby simultaneously facilitating severing of the interconnecting sutures and any tissue ingrowth which may have formed between the sewing ring and valve assembly as the blade is worked around through the cutting path.

7 Claims, 2 Drawing Sheets

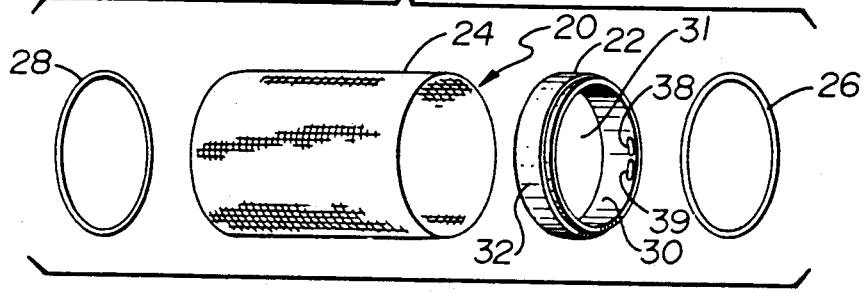
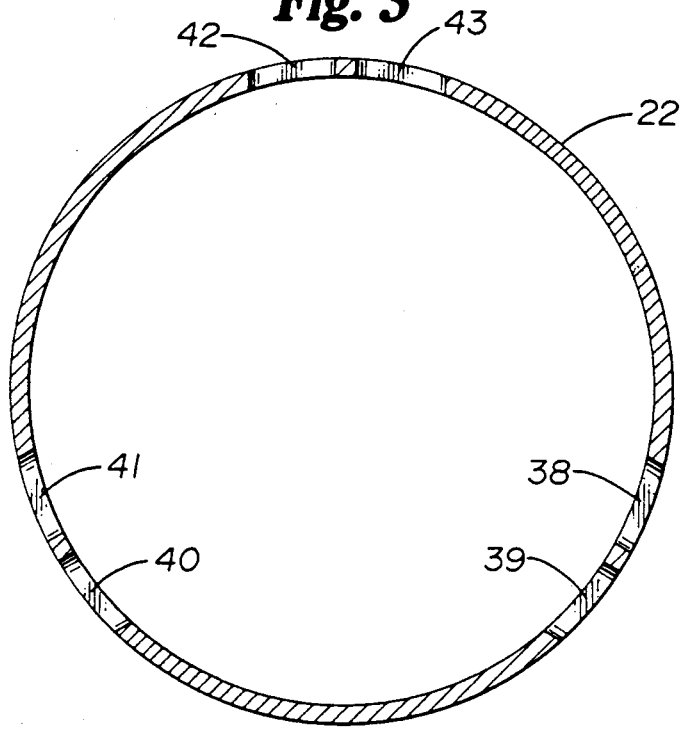
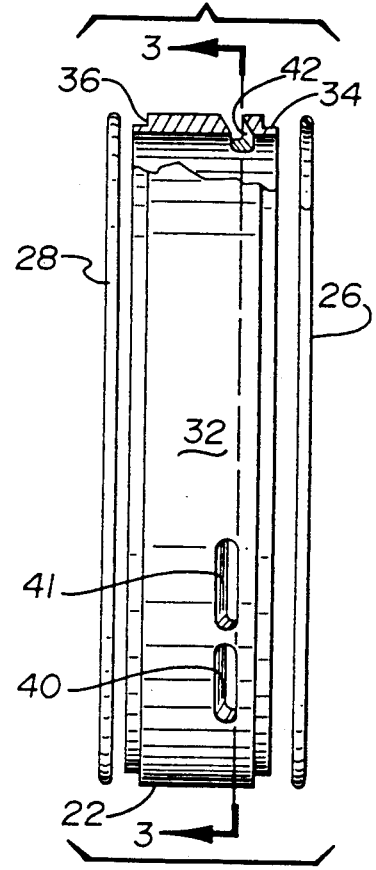
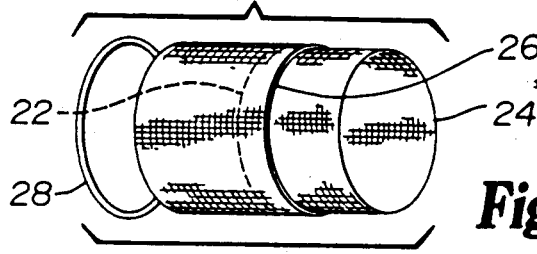
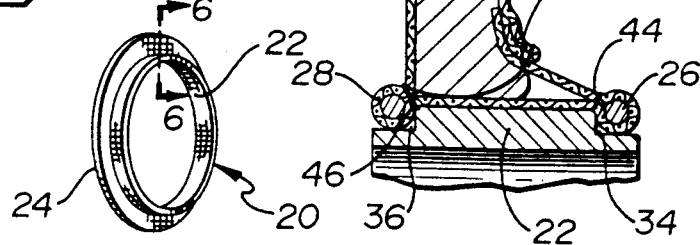
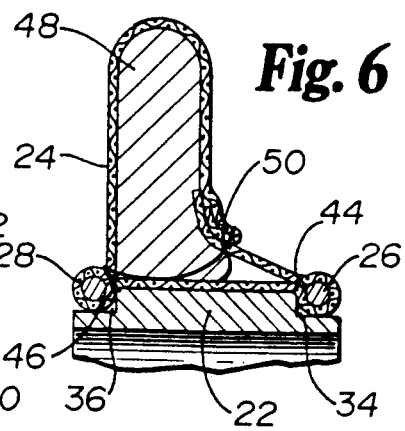

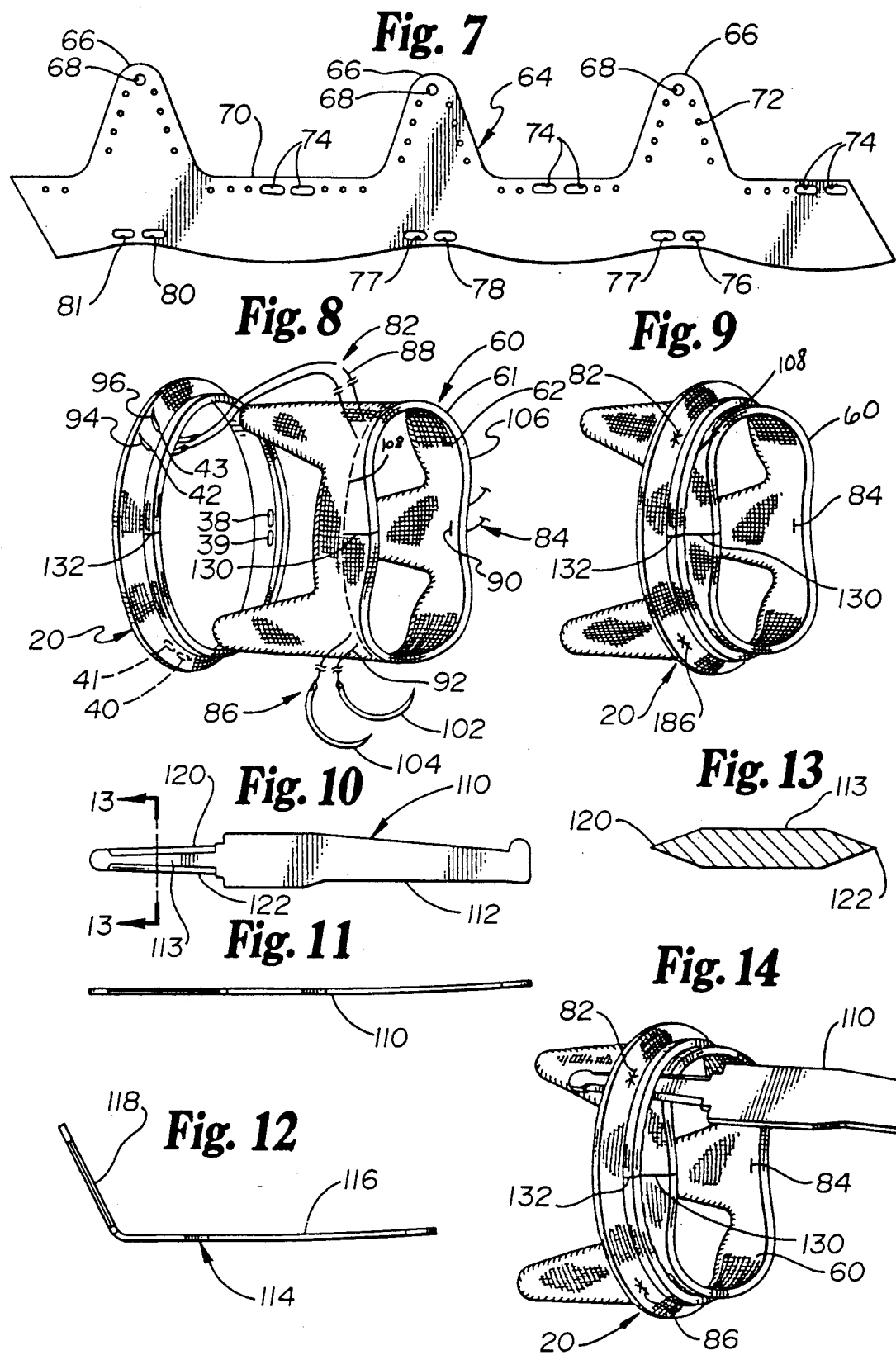

HEART VALVE PROSTHESIS

BACKGROUND OF THE INVENTION

1. Field of the Invention

The present invention relates to prosthetic heart valves. More particularly, the present invention is directed to heart valves of the type including sewing ring to be permanently mounted in the heart and a removable valve member mounted in the sewing ring.

2. Description of the Prior Art

Typical prior art prosthetic heart valves are essentially permanently installed. Both mechanical valves and tissue valves are sutured into place. These valves are further fixed in place by ingrowth of tissue on the perimeter.

Of course it is not possible to design a prosthetic heart valve that will last forever. All valves have some natural life. At the end of the life cycle, it is appropriate to remove the prosthetic valve and replace it with a successor valve. Additionally, children require replacement of valves because of changes in their heart size as they grow.

The replacement of the heart valve can be difficult. Because of tissue ingrowth, the surgery required to remove the implanted heart valve and implant the successive replacement can be more complex than the original implantation operation.

Attempts have been made to ease this replacement by providing heart valves with replaceable elements. For example, U.S. Pat. No. 3,997,923 to Possis discloses one attempt to solve this problem by having a removable valve member snapped into a permanent sewing ring. This type of attachment mechanism is susceptible to overgrowth by tissue, which impedes removal. An improvement on this mechanism is shown in U.S. Pat. No. 4,680,031 to the present inventor. In that case, a valve member was removably threaded onto a permanent sewing ring.

A further goal of prosthetic heart valves is to increase blood flow through the valve. A valve which offers the least obstruction to the flow of blood maximizes cardiac output. Previous sewing rings have considerably narrowed the opening through which blood flows. It is desirable to cover as little possible of the natural opening of the heart with the sewing ring and valve mechanism.

A valve according to the present invention improves on the prior art by providing a more easily removable valve member, as well as maximizing the open bore of the heart valve.

SUMMARY OF THE INVENTION

A prosthetic heart valve according to the present invention comprises a sewing ring and removable valve member. The sewing ring is designed for permanent attachment to heart tissue. The valve member is formed for slidable engagement in a central bore of the sewing ring. The valve is then fixed in place in the ring by attachment means such as sutures.

The valve member is removed by inserting a scalpel between the sewing ring and the valve member and cutting a circular path between the two. The scalpel cuts any tissue ingrowth and the attaching sutures so that the valve member may be slid out of the sewing ring. A replacement valve member is then slidably mounted in the attached sewing ring and is connected by suture means.

The sewing ring is formed from a generally cylindrical main ring which is provided with two annular grooves in the outer wall. The grooves are preferably shoulders at the edges of the main ring. First and second O-rings are sized to engage in the first and second grooves.

A cloth, which is preferably tubular, is mounted over the main ring. First and second O-rings are mounted over the cloth in the grooves. The cloth is then folded over the O-rings and sewn to itself so that the O-rings are held against the main ring.

A scalpel is disclosed for cutting tissue and sutures between the sewing ring and the valve member. The scalpel has first and second cutting edges so that cutting may be done in either direction. The scalpel is sized for fitting in the narrow circular path between the sewing ring and the valve member.

In one embodiment, the scalpel includes a bend of approximately 60 degrees so that the scalpel may be employed on sewing rings mounted in the mitral position.

A prosthetic heart valve constructed according to the present invention solves many of the problems associated with prior art heart valves. The previous recognition that a two piece replaceable valve is desirable has proven difficult to implement. Tissue ingrowth in the heart has prevented full realization of the hope for removable two piece valves. The present invention provides novel apparatus and method for separating the valve member from the tissue ingrowth so that removal from the sewing ring is eased.

The sewing ring employed in the present invention has a narrow wall profile which maximizes the open area available for mounting the valve member. The larger opening available for the valve member means that there is a larger area available for blood flow within the valve member. This maximization of valve size and bore opening improves hemodynamics.

BRIEF DESCRIPTION OF THE DRAWINGS

FIG. 1 is an exploded perspective view of a sewing ring according to the present invention.

FIG. 2 is a side view, partially cutaway, of the main ring and first and second O-rings of the sewing ring of FIG. 1.

FIG. 3 is a cross sectional view taken on line 3—3 of FIG. 2.

FIG. 4 is a perspective view of the sewing ring of FIG. 1, partially assembled.

FIG. 5 is a perspective view of the completed sewing ring of the type illustrated in FIGS. 1-4.

FIG. 6 is a cross sectional view taken on line 6—6 of FIG. 5.

FIG. 7 is a side elevational view of a blank for a stent.

FIG. 8 is a perspective view of a completed stent made of the blank of FIG. 7 being mounted by sutures in the sewing ring of FIGS. 1-6.

FIG. 9 shows a completed valve after mounting as shown in FIG. 8.

FIG. 10 shows a scalpel designed for removing the stent from the sewing ring after implantation.

FIG. 11 is a side view of the scalpel of FIG. 10.

FIG. 12 is a side view of a second embodiment of the scalpel according to the present invention.

FIG. 13 is a cross sectional view taken on line 13—13 of FIG. 10.

FIG. 14 is a perspective view showing the scalpel of FIG. 10 in operation on the valve of FIG. 9.

DETAILED DESCRIPTION OF THE DRAWINGS

A sewing ring 20 constructed according to the present invention comprises a main ring 22, cloth 24 and first and second O-rings 26 and 28, respectively. Main ring 22, in this embodiment, is a short cylinder having an inside wall 30, forming bore 31, and outer wall 32. Main ring 22 has first and second shoulders or grooves 34 and 36, respectively. First and second shoulders 34 and 36 are sized to receive first and second O-rings 26 and 28, respectively.

Main ring 22 carries means for attaching heart valves. In the illustrated embodiment, this includes three pairs of slots 38-43.

Main ring 22 is preferably made of cobalt material, such as Stellite 25. Other biocompatible metals such as titanium may also be used. Of course, the size, both in diameter and height of the cylinder, varies with the application. For example, mitral valve rings preferably employ a wider cylinder than aortic valve rings.

The thickness of material used in main ring 22 is approximately 0.020 inch. The ring is manufactured by conventional methods such as machining it out of a bar of metal or by cutting a tube. Shoulders 34 and 36 are machined in.

Slots 38-43 are preferably cut in main ring 32 by electrical discharge machining (EDM). Other methods could be used to cut slots 38-43, such as lasers. After cutting, the edges of slots 38-43 are polished so as not to cut sutures inserted through them. All edges are contoured so as to provide a rounded running surface for sutures.

Cloth 24 is preferably a cylinder of material such as Dacron ® or Teflon ®. Any of the various well known materials used in the industry for sewing valves may be employed in practicing the present invention.

Assembly of sewing ring 20 is illustrated by the partially assembled view in FIG. 4. Main ring 22 is positioned inside cloth tube 24. The exact positioning of main ring 22 longitudinally within cloth 24 depends upon the application. O-rings 26 and 28 are slid over the outside of cloth tube 24 until they engage shoulders 34 and 36, respectively.

In FIG. 4, O-ring 26 is shown in place. The outline of main ring 22 is shown in dotted lines in FIG. 4. O-ring 28 is shown in position to be mounted over cloth 24.

After the mounting of O-ring 26, cloth 24 is inverted over O-ring 26 and stitched to itself as illustrated by stitch 44 in FIG. 6. The opposite end of cloth 24 is inverted over O-ring 28 and stitched to itself as illustrated by stitch 46 in FIG. 6. This locks O-rings 26 and 28 in place on shoulders 34 and 36, respectively.

The ends of cloth 24 are turned in and stitched in place to form what is sometimes known in the industry as the sewing ring. This protrusion is used to sew the assembled ring 20 to tissue.

In certain applications, such as the mitral position, a larger sewing protrusion is needed. In these cases, as in the illustrated embodiment, filler or pad 48 is added. Pad 48 may be any of the common sewing ring fabrics such as foam or batting material. Pad 48 is circumferentially placed around main ring 24 outside of cloth 24. Cloth 24 is then wrapped, as illustrated in FIG. 6, around pad 48 and stitched in place by stitches 50. In this embodiment, stitches 44 and 46 may be basting stitches which are removed once O-rings 26 and 28 are firmly held in place by stitches 50. Various standard stitching techniques may be used to fix cloth 24 around O-rings 26 and 28.

FIG. 5 illustrates a completed sewing ring of the type having a shoulder pad 48.

The sewing ring of the present invention may be used with various removable valve mechanisms constructed according to the present invention. Either mechanical or tissue valves may be employed. The illustrated valve mechanism is a tissue valve 60. Valve 60 comprises stent 61 which is covered by cloth 62. Cloth 62 may be any of the various materials used for cloth 24. The stent 61 is formed of an Elgiloy ® plate 64, illustrated in flat form in FIG. 7. Construction of stent 61 employs manufacturing techniques disclosed in U.S. Pat. No. 4,680,031, which is incorporated herein. Plate 64 is formed into a cylinder and covered with cloth 62 as illustrated. Plate 64 has three commissures 66, each carrying a mounting hole 68. Along upper edge 70 of plate 64 lie suturing holes 72 and three pair of attachment slots 74.

Also provided on plate 64 are attachment means for mounting stent 61 in sewing ring 20. In the illustrated embodiment, the attachment means includes three pair of slots 76-81 which are positioned to align with slots 38-43, respectively, in sewing ring 20.

In the illustrated embodiment, the attachment means further includes three double needle suture sets 82, 84 and 86. The sets comprise suture pairs 88, 90 and 92, respectively, and needle pairs 94, 96, 98 (not illustrated), 100 (not illustrated), 102 and 104, respectively.

The illustrated stent is designed for mounting a tissue valve, such as a porcine valve. The invention is also practiced by configuring a mechanical valve in this shape for slidable mounting, with attachment means suitable for connecting to sewing ring 20. The interchangeability of tissue and mechanical valves is an advantage of this system. For example, in certain situations it is not possible to give anticoagulants to the patient because of pregnancy or other physical conditions. Since anticoagulants are normally prescribed in conjunction with implantation of a mechanical valve, a tissue valve is usually used in these situations. At a later time when anticoagulants may be administered, the tissue valve may be replaced with a mechanical valve.

Using the present invention, mechanical and tissue valves may be interchanged using the permanently implanted sewing ring 20. In situations where the conditions requiring a tissue valve no longer exist, a mechanical valve may be used as a replacement.

For construction of a two piece valve according to the present invention, valve member 60 is positioned relative to sewing ring 20, as illustrated in FIG. 8. Needles 94 and 96 are inserted through slots 42 and 43 and sewing ring 20, as illustrated. Needles 98 and 100 (not illustrated) are inserted through slots 38 and 39. Needles 102 and 104 are then inserted through slots 40 and 41 in stent 20. The needles 94-104 are then pulled up to snug the sutures 82-86 down while valve member 60 is inserted in sewing ring 20.

It is important that valve members such as stent 61 not be allowed to pass through sewing ring 20. Means are provided to prevent movement of stent 61 past the point of alignment in valve 20. In the present invention, stitch 108 is taken in cloth 24 around the circumference of valve 60, as illustrated in FIG. 8. This ridge provides sufficient tension so that valve 60 cannot pass through sewing ring 20. Of course, other embodiments may be used to prevent excess movement of a valve member into stent 20. For example, the cylinder of stent 61 may be tapered to prevent movement through ring 20.

Stent 61 is sized relative to the sewing ring 20 so that slots 76-81 of stent 61 align with slots 38-43 of sewing ring 20. Thus, when suture sets 82, 84 and 86 are tightened, all slots are in proper alignment. The suture sets 82, 84 and 86 are tied tightly and trimmed, as illustrated in FIG. 9. Valve member 60 is now firmly mounted in sewing ring 20.

Implantation in the heart is by known prior art methods. Cloth 24, including pad 48 if present, is sewn to the heart to hold sewing ring 20 in place. As is well known in the art, tissue grows over cloth 24 to further fix sewing ring 20 in place.

Tissue may grow around the union between stent 60 and sewing ring 24 as part of the body's natural process of covering foreign objects. In order to remove valve member 60 of the two-piece valve, it is necessary to remove any tissue ingrowth. Such removal is much eased by a scalpel 110 constructed according to the present invention.

Scalpel 110 is preferably formed from stainless steel. It includes a handle 112 and blade 113. Two configurations are designed for use with valves for different applications. Blade 110, as illustrated, is useful to remove the aortic valve and the inferior portion of the mitral valve. A second embodiment 114 includes a bend of approximately a 60° angle between handle 116 and blade 118. This angled scalpel 114 is used for the posterior portion of the mitral valve. The blade is sized to fit between sewing ring 20 and valve member 60, and is preferably less than 0.005 inches thick.

Blade 113 includes first and second edges 120 and 122 so that blade 113 cuts in either direction. Blade 113 is tapered slightly and sized sufficiently thin so that it can follow the circular path between wall 30 of sewing ring 26 and valve member 60.

As illustrated in FIG. 14, scalpel 110 is slipped between valve member 60 and sewing ring 20. Scalpel 110 is slowly worked around the circumference of stent 60. In the process, scalpel 110 cuts any tissue ingrowth which is formed around the union of stent 60 and sewing ring 20. Scalpel 110 also cuts suture pairs 82, 84 and 86. Stent 60 may then be easily slid out of sewing ring 20. Other means may be used to cut tissue from between sewing ring 20 and valve member 60, such as a laser cutter.

In order to simplify the insertion process, marking means are included for alignment of valve member 60 with sewing ring 20. In the illustrated embodiment, the marking means is a line 130 on the valve member 60 which aligns with a line 132 on sewing ring 20. Other marking means could be used such as notches in stent 61 of valve member 60 and sewing ring 20.

While this invention has been disclosed in terms of the illustrated embodiments, it is to be understood that many other embodiments can be constructed employing the present invention.

What is claimed is:

1. A prosthetic heart valve comprising:
   a sewing ring having a main ring forming a central bore, the ring having an inner surface towards the central bore and an outer surface, the outer surface including two annular grooves;
   first and second O-rings sized to fit the two grooves on the main ring;
   cloth for forming a sewing ring, mounted by first surrounding the ring, then by having the cloth held to the ring by mounting the first and second O-rings over the cloth, and the cloth being sewn in place around the O-rings on the outer surface of the ring; and
   a valve member mounted within said central bore.

2. A sewing ring for a prosthetic heart valve comprising:
   a ring forming a central bore, the ring having an inner surface towards the central bore and an outer surface, the outer surface including first and second annular grooves;
   first and second O-rings sized to fit the two grooves on the ring; and
   cloth for forming a sewing ring, mounted by first surrounding the ring, then by having the cloth held to the ring by mounting the O-rings over the cloth in the grooves, and the cloth being sewn in place around the O-rings on the outer surface of the ring.

3. A method of making a sewing ring for a prosthetic heart valve;
   providing a generally cylindrical main ring having an inner surface forming a central bore therethrough, and an outer surface having first and second annular grooves;
   mounting cloth over the ring so that it contacts the outer surface;
   mounting a first O-ring over the cloth onto the first groove in the ring, securing the cloth to the main ring;
   mounting a second O-ring over the cloth in the second groove, securing the cloth to the main ring; and
   folding the cloth over each O-ring and suturing the cloth to retain the O-rings on the main ring.

4. A method for replacing a prosthetic heart valve having a permanent sewing ring sutured to a patient and a replaceable valve element slidably mounted in and sutured to the sewing ring, comprising the following steps:
   surgically exposing in the patient said prosthetic heart valve;
   inserting a scalpel in the space within the bore of the sewing ring and outside said valve element so that the scalpel extends through any tissue grown across the sewing ring and onto said valve element;
   cutting a circular path around the outside of said valve element, severing any tissue attaching said valve element to said sewing ring and severing sutures attaching said valve element to said sewing ring;
   removing said valve element from said sewing ring;
   slidably inserting a replacement valve element into said sewing ring; and
   suturing said replacement valve element to said sewing ring.

5. A prosthetic heart valve comprising:
   a generally solid sewing ring having means for attachment to human tissue, said ring having a wall defining a central generally cylindrical bore therethrough devoid of inwardly directed projections, said bore having an interior diameter;
   valve means for controlling blood flow through said heart valve, said valve means having a generally cylindrical outer wall devoid of outwardly directed projections, said outer wall having an exterior diameter which is less than said interior diameter to allow said valve means to be slidably removably mounted within the bore of said sewing ring; and means for attaching said valve means to said sewing ring, said attachment means including sutures extending from said wall of said sewing ring to said wall of said valve means to hold said valve means in place within said sewing ring, such that said outer wall of said valve means is mounted in spaced-apart relationship from said wall of said sewing ring to define a generally cylindrical cutting path therebetween.

6. The prosthetic heart valve of claim 5 wherein said wall of said sewing ring comprises a rigid structure made of a metal.

7. The prosthetic heart valve of claim 6 wherein said attachment means include openings extending through the wall of said sewing ring and being located at circumferentially spaced-apart locations about said sewing ring to receive said correspondingly located sutures extending from said wall of said valve means.

* * * * *